United States Patent
Bae et al.

(10) Patent No.: US 9,650,420 B2
(45) Date of Patent: *May 16, 2017

(54) PEPTIDES FOR PREVENTING OR TREATING BONE DISEASES AND USE THEREOF

(71) Applicant: KYUNGPOOK NATIONAL UNIVERSITY INDUSTRY—ACADEMIC COOPERATION FOUNDATION, Daegu (KR)

(72) Inventors: Jae Sung Bae, Daegu (KR); Hee Kyung Jin, Daegu (KR); Min Hee Park, Gyeongsangbuk-do (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/937,317

(22) Filed: Nov. 10, 2015

(65) Prior Publication Data

US 2017/0081367 A1 Mar. 23, 2017

Related U.S. Application Data

(63) Continuation of application No. 14/861,663, filed on Sep. 22, 2015.

(51) Int. Cl.
| | | |
|---|---|---|
| *A61K 38/10* | (2006.01) | |
| *A61K 38/22* | (2006.01) | |
| *C07K 7/08* | (2006.01) | |
| *A61P 19/10* | (2006.01) | |
| *A61K 38/00* | (2006.01) | |

(52) U.S. Cl.
CPC ........... *C07K 7/08* (2013.01); *A61K 38/10* (2013.01); *A61K 38/2271* (2013.01); *A61K 38/00* (2013.01)

(58) Field of Classification Search
None
See application file for complete search history.

(56) References Cited

U.S. PATENT DOCUMENTS

2006/0247156 A1* 11/2006 Vanderby ............. A61K 38/046
514/11.1

FOREIGN PATENT DOCUMENTS

KR 10-2009-0119718 11/2009

OTHER PUBLICATIONS

Margulies et al., Clin. Orthop. Relat. Res., 1996, vol. 324:145-152 (abstract).*
Baldock, et al., "Neuropeptide Y Knockout Mice Reveal a Central Role of NPY in the Coordination of Bone Mass to Body Weight," PLoS ONE, vol. 4, Issue 12, e8415, 9 pages (Dec. 2009).
Lee, et al., "NPY regulation of bone remodelling," Neuropeptides 43; pp. 457-463 (2009).

* cited by examiner

*Primary Examiner* — Xiaozhen Xie
(74) *Attorney, Agent, or Firm* — Marshall, Gerstein & Borun LLP

(57) ABSTRACT

The present disclosure relates to a novel peptide for preventing or treating bone diseases. Further, the present disclosure relates to a polynucleotide encoding the peptide, a vector including the polynucleotide, a host cell transformed by the vector, and a method for producing the peptide by using the host cell. Furthermore, the present disclosure relates to a composition for preventing or treating bone diseases, including the novel peptide. The novel peptide according to the present disclosure induces mobilization of hematopoietic stem cells to blood and causes a decrease in the number of osteoclasts, and, thus, decreases bone erosion caused by osteoclasts, thereby suppressing progress of an osteoporotic lesion. Further, the novel peptide is safe since it does not cause rejection in the body. Furthermore, since the novel peptide is formed of 15 short amino acids, a low dose of the peptide can relieve symptoms of osteoporosis.

3 Claims, 11 Drawing Sheets

SEQUENCE LISTING

```
<160> NUMBER OF SEQ ID NOS: 15

<210> SEQ ID NO 1
<211> LENGTH: 15
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Osteopep1

<400> SEQUENCE: 1

Asp Asn Pro Gly Glu Asp Ala Pro Ala Glu Asp Met Ala Arg Tyr
1               5                   10                  15

<210> SEQ ID NO 2
<211> LENGTH: 21
<212> TYPE: DNA
<213> ORGANISM: Artificial Sequence
<220> FEATURE:
<223> OTHER INFORMATION: Synthetic primer

<400> SEQUENCE: 2
ttcctatcag agcccataga g                                           21

<210> SEQ ID NO 3
<211> LENGTH: 20
<212> TYPE: DNA
<213> ORGANISM: Artificial Sequence
<220> FEATURE:
<223> OTHER INFORMATION: Synthetic primer

<400> SEQUENCE: 3
ccagaccatc ctggataatg                                             20

<210> SEQ ID NO 4
<211> LENGTH: 23
<212> TYPE: DNA
<213> ORGANISM: Artificial Sequence
<220> FEATURE:
<223> OTHER INFORMATION: Synthetic primer

<400> SEQUENCE: 4
ccaaaagcaa agccaattac aag                                         23
```

<210> SEQ ID NO 5
<211> LENGTH: 20
<212> TYPE: DNA
<213> ORGANISM: Artificial Sequence
<220> FEATURE:
<223> OTHER INFORMATION: Synthetic primer

<400> SEQUENCE: 5
agactcgggc ctacaatgga                                            20

<210> SEQ ID NO 6
<211> LENGTH: 18
<212> TYPE: DNA
<213> ORGANISM: Artificial Sequence
<220> FEATURE:
<223> OTHER INFORMATION: Synthetic primer

<400> SEQUENCE: 6
acgggggtca attctaag                                              18

<210> SEQ ID NO 7
<211> LENGTH: 18
<212> TYPE: DNA
<213> ORGANISM: Artificial Sequence
<220> FEATURE:
<223> OTHER INFORMATION: Synthetic primer

<400> SEQUENCE: 7
gccattcctg actccaca                                              18

<210> SEQ ID NO 8
<211> LENGTH: 20
<212> TYPE: DNA
<213> ORGANISM: Artificial Sequence
<220> FEATURE:
<223> OTHER INFORMATION: Synthetic primer

<400> SEQUENCE: 8
aaaagcggag acaggagaca                                            20

<210> SEQ ID NO 9
<211> LENGTH: 20
<212> TYPE: DNA
<213> ORGANISM: Artificial Sequence
<220> FEATURE:
<223> OTHER INFORMATION: Synthetic primer

<400> SEQUENCE: 9
agcacgagaa gctcaggaga                                            20

<210> SEQ ID NO 10
<211> LENGTH: 20
<212> TYPE: DNA
<213> ORGANISM: Artificial Sequence
<220> FEATURE:
<223> OTHER INFORMATION: Synthetic primer

<400> SEQUENCE: 10
attgaacctg cagaccaagc                                            20

<210> SEQ ID NO 11
<211> LENGTH: 20
<212> TYPE: DNA
<213> ORGANISM: Artificial Sequence
<220> FEATURE:

<223> OTHER INFORMATION: Synthetic primer

<400> SEQUENCE: 11
gcaacagaac aaggatcagg                                              20

<210> SEQ ID NO 12
<211> LENGTH: 30
<212> TYPE: DNA
<213> ORGANISM: Artificial Sequence
<220> FEATURE:
<223> OTHER INFORMATION: Synthetic primer

<400> SEQUENCE: 12
tgtggagttt tagagatatt agatagtggg                                   30

<210> SEQ ID NO 13
<211> LENGTH: 28
<212> TYPE: DNA
<213> ORGANISM: Artificial Sequence
<220> FEATURE:
<223> OTHER INFORMATION: Synthetic primer

<400> SEQUENCE: 13
aacacactct taacaccact aaatcacc                                     28

<210> SEQ ID NO 14
<211> LENGTH: 21
<212> TYPE: DNA
<213> ORGANISM: Artificial Sequence
<220> FEATURE:
<223> OTHER INFORMATION: Synthetic primer

<400> SEQUENCE: 14
ttgctgttga agtcgcagga g                                            21

<210> SEQ ID NO 15
<211> LENGTH: 20
<212> TYPE: DNA
<213> ORGANISM: Artificial Sequence
<220> FEATURE:
<223> OTHER INFORMATION: Synthetic primer

<400> SEQUENCE: 15
tgtgtccgtc gtggatctga                                              20

PEPTIDES FOR PREVENTING OR TREATING BONE DISEASES AND USE THEREOF

This is a continuation of U.S. patent application Ser. No. 14/861,663, filed Sep. 22, 2015.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: ASCII (text) file named "40064A_SubSeqListing.txt," 633 bytes, created on Nov. 9, 2015.

TECHNICAL FIELD

The present disclosure relates to a novel peptide for preventing or treating bone diseases and a polynucleotide encoding the same.

Further, the present disclosure relates to a method for treating a target with a bone disease by using the peptide.

BACKGROUND

Osteoporosis can be classified into postmenopausal osteoporosis and senile osteoporosis. Postmenopausal osteoporosis occurs due to an increase in bone resorption caused by activation of an osteoclast arising from a rapid hormonal change caused by menopause. Further, senile osteoporosis occurs due to a decrease in bone formation caused by a decrease in a function of an osteoblast caused by aging. Bone fractures caused by osteoporosis lead to severe restriction on activity. In particular, hip fracture is involved in high mortality of about 15 to 35%. Therefore, it is important to diagnose and treat osteoporosis prior to occurrence of osteoporotic fractures.

Conventionally, bisphosphonate-based medicines have been known as medicines for treating osteoporosis. It is known that bisphosphonate sticks to an inorganic element of bone and when an osteoclast resorbs the bone to which bisphosphonate sticks, a non-hydrolyzed ATP analogue is formed and exhibits toxicity on the cell or causes a decrease in activity of the osteoclast and apoptosis in various ways in the osteoclast, thereby reducing bone resorption and thus increasing a bone density. Although such medicines have been known as being relatively safe, there have been recently suggested that when being used for a long time, the medicines may affect remodeling of bone by normal bone resorption or bone formation, or healing of bone after fracture, resulting in a decrease in bone elasticity and a bad effect on bone strength. There is a report that the medicines actually cause stress fractures in numerous patients.

Accordingly, development of novel bone metabolism involved in occurrence of osteoporosis and development of a medicine for preventing or treating osteoporosis has been desperately needed.

A bone marrow stem cell niche is defined as a molecular microenvironment where cells' functions and fates are regulated by interactions between various cells including a bone marrow stem cell present in bone marrow. So far, there have been known roughly two kinds of bone marrow stem cell niches including "endosteal niche" and "perivascular niche".

Firstly, "endosteal niche" refers to a microenvironment where basal cells are present in bone marrow, and basal cells, osteoblasts, and osteoclasts are mainly present. In the endosteal niche, these cells are adjacent to other cells, particularly hematopoietic progenitor cells (HPCs) or hematopoietic stem cells (HSCs) by intracellular adhesion factors (CXCL12, Ang-1, VCAM1, stem cell factor, IL-7, and the like), and the hematopoietic stem cells sticking to the osteoblasts are mobilized to blood in response to a neurotransmission signal from the outside or homed to the bone marrow so as to affect homeostatic maintenance in the bone marrow.

Further, "perivascular niche" refers to a microenvironment constituted by macrophages, bone marrow mesenchymal stem cells (MSCs), and CAR cells (CXCL12 abundant reticular cells). In the perivascular niche, these cells are adjacent to hematopoietic cells by intracellular adhesion factors and the hematopoietic stem cells sticking to the macrophages and the bone marrow mesenchymal stem cells are mobilized to blood in response to a neurotransmission signal, such as stress or a neurotransmitter, from the outside in a similar manner to the endosteal niche.

As described above, the bone marrow stem cells are mobilized to a bloodstream or homed in the bone marrow niche. Mobilization of bone marrow stem cells to blood is an important phenomenon occurring in bone marrow when the body is stressed or damage, and refers to a phenomenon in which stem cells, immune-related cells, and osteoclasts move from bone marrow to a blood vessel. The cells mobilized to the blood vessel move along a blood stream to a lesion site and help to heal the lesion. Meanwhile, the bone marrow stem cells that finish the healing action in the lesion site return to the bone marrow along the blood stream, and such a phenomenon is referred to as "homing".

A bone marrow hematopoietic stem cell can be differentiated into lymphoid cells and myeloid cells in bone marrow. An osteoclast as one of the myeloid cells differentiated from the bone marrow hematopoietic stem cell maintains bone formation and bone erosion through a balance between the osteoclast and an osteoblast in the bone marrow. If such a balance is broken, there is an increase in the number of osteoclasts and an increase in a speed of bone erosion, resulting in occurrence of osteoporosis.

It is known that if S1P (sphingosine-1-phosphate) as a material for inducing mobilization of osteoclast precursors to blood is administered or an S1P receptor agonist (FTY720) is administered in order to decrease the number of osteoclasts in bone marrow, there is an increase in bone formation. Likewise, if mobilization of bone marrow hematopoietic stem cells as primitive cells for osteoclasts to blood is induced, there is a decrease in differentiation into osteoclasts, and, thus, the number of osteoclasts in bone marrow is decreased.

The inventors of the present disclosure have carefully tried to discover a novel active molecule which can be used for treating osteoporosis. As a result thereof, the inventors of the present disclosure found that a short peptide having a specific sequence induces mobilization of hematopoietic stem cells to blood as described above and causes a decrease in the number of osteoclasts, and, thus, decreases bone erosion caused by osteoclasts, thereby suppressing progress of an osteoporotic lesion, and denominated the peptide as "Osteopep1".

SUMMARY

The present disclosure has been made in an effort to provide a novel peptide for preventing or treating bone diseases.

Further, the present disclosure has been made in an effort to provide a polynucleotide encoding the peptide.

Furthermore, the present disclosure has been made in an effort to provide a method for treating a target with a bone disease by using the peptide.

An exemplary embodiment of the present disclosure provides a peptide for preventing or treating a bone disease, the peptide having an amino acid sequence of SEQ ID NO: 1.

Hereinafter, the present disclosure will be described in detail.

The peptide of the present disclosure is a novel peptide having an amino acid sequence described below, and the inventors of the present disclosure denominated the peptide as "Osteopep1".

Asp-Asn-Pro-Gly-Glu-Asp-Ala-Pro-Ala-Glu-Asp-Met-Ala-Arg-Tyr (SEQ ID NO: 1)

Further, the peptide of the present disclosure has the above-described specific sequence, and includes a peptide further including 1 to 50 amino acids at an N-terminal and/or a C-terminal.

The above-described novel peptide provided in the present disclosure may be used for preventing or treating a bone disease. The bone disease is not limited in kind, but may be osteoporosis, osteomalacia, rickets, fibrous ostitis, an adynamic bone disease, and a metabolic bone disease, and most preferably, osteoporosis.

The novel peptide decreases an expression level of an adhesion factor for a bone marrow hematopoietic stem cell, mobilizes the bone marrow hematopoietic stem cell in bone marrow to a bloodstream, and, thus, decreases osteoclasts in the bone marrow. Further, the peptide induces mobilization of the hematopoietic stem cell to blood and causes a decrease in the number of osteoclasts, and, thus, decreases bone erosion caused by osteoclasts, thereby suppressing progress of an osteoporotic lesion. Furthermore, the peptide is safe since it does not cause rejection in the body. Furthermore, since the peptide is formed of 15 short amino acids, a low dose of the peptide can relieve symptoms of osteoporosis.

The peptide may be an artificially produced peptide or a recombinant peptide.

Another exemplary embodiment of the present disclosure provides a polynucleotide encoding the peptide.

The term "polynucleotide" refers to a polymer of deoxyribonucleotide or ribonucleotide that exists in a single-stranded form or a double-stranded form. The term "polynucleotide" comprehensively includes a RNA genome sequence and a RNA sequence transcribed from a DNA (gDNA and cDNA), and unless the context clearly indicates otherwise, includes an analogue of natural polynucleotide.

The polynucleotide may include, in addition to a nucleotide sequence encoding the peptide, a complementary sequence to the nucleotide sequence. The complementary sequence may include not only a perfectly complementary sequence, but also a substantially complementary sequence to the nucleotide sequence. The complementary sequence means a sequence that can be hybridized with a nucleotide sequence that encodes the peptide of SEQ ID NO: 1 under stringent conditions known in the art.

Further, the polynucleotide may be changed. The change includes an addition, a deletion, or a non-conservative substitution or a conservative substitution of a nucleotide. The polynucleotide encoding the amino acid sequence may be interpreted as including a nucleotide sequence exhibiting a substantial identity with respect to the nucleotide sequence. The substantial identity aligns the nucleotide sequence and another random sequence in a way that they are maximally correspondent, and when the aligned sequence is analyzed using an algorithm generally used in the art, the sequence may exhibit greater than 80% identity, greater than 90% identity, or greater than 95% identity.

Furthermore, the present disclosure may provide a vector including the polynucleotide, a host cell transformed by the vector, and a method for producing the peptide using the host cell.

The term "vector" refers to a method for expressing a target gene in a host cell. For example, the term "vector" includes a plasmid vector, a cosmid vector, and a viral vector such as a bacteriophage vector, an adenovirus vector, a retrovirus vector, and an adeno-associated virus vector. The recombinant vector may be prepared by modifying the following: a plasmid (for example, pSC101, pGV1106, pACYC177, ColE1, pKT230, pME290, pBR322, pUC8/9, pUC6, pBD9, pHC79, pIJ61, pLAFR1, pHV14, a series of pGEX, a series of pET, and pUC19, and the like), a phage (for example, λgt4λB, λ-Charon, λΔz1, and M13, and the like), or a virus (for example, CMV, SV40, and the like), which are often used in the art.

In the recombinant vector, the polynucleotide that encodes the amino acid sequence of SEQ ID NO: 1 may be operatively linked to a promoter. The term "operatively linked" used herein refers to a functional binding between a nucleotide expression regulatory sequence (for example, a promoter sequence) and another nucleotide sequence. Therefore, the regulatory sequence may regulate the transcription and/or translation of the other nucleotide sequence.

Typically, the recombinant vector may be constructed as a vector for cloning or a vector for expression. The vector for expression may be a vector that is normally used in the art for expression of a foreign protein in plants, animals, or microorganisms. The recombinant vector may be constructed through various methods known in the art.

The recombinant vector may be constructed for use in prokaryotic or eukaryotic host cells. For example, if the recombinant vector is an expression vector and a prokaryotic cell is used as a host cell, the recombinant vector may in general include a strong promoter for transcription (for example, a pLλ promoter, a trp promoter, a lac promoter, a tac promoter, a T7 promoter, and the like), a ribosome binding site for initiating translation, and a transcription/translation termination sequence. If a eukaryotic cell is used as a host cell, an origin of replication operating in an eukaryotic cell included in a vector may be a fl replication origin, a SV40 replication origin, a pMB1 replication origin, an adeno replication origin, an AAV replication origin, a CMV replication origin, a BBV replication origin, and the like, but is not limited thereto. Further, the promoter used in the recombinant vector may be a promoter derived from a genome of a mammal cell (for example, a metallothionine promoter) or a promoter derived from a virus of a mammal cell (for example, an adenovirus anaphase promoter, a vaccinia virus 7.5K promoter, an SV40 promoter, a cytomegalo virus (CMV) promoter, or a tk promoter of HSV), and may in general include a polyadenylated sequence as a transcription termination sequence.

Further, the present disclosure may provide a host cell transformed by the recombinant vector.

The host cell may be any host cell known in the art. Examples of the prokaryotic cell include *E. coli* JM109, *E. coli* BL21, *E. coli* RR1, *E. coli* LE392, *E. coli* B, *E. coli* X 1776, *E. coli* W3110, strains of *Bacillus* species such as *Bacillus subtillis* or *Bacillus thuringiensis*, and intestinal bacteria and strains such as *Salmonella typhymurium*, *Ser-*

*ratia marcescens*, and various *Pseudomonas* species. When transformation is performed using a eukaryotic cell, a host cell may be *Saccharomyce cerevisiae*, an insect cell, a plant cell, or an animal cell, and may include, for example, SP2/0, CHO(Chinese hamster ovary) K1, CHO DG44, PER.C6, W138, BHK, COS-7, 293, HepG2, Huh7, 3T3, RIN, MDCK cell lines, and the like.

Furthermore, the present invention may provide a method for producing a peptide for preventing or treating bone diseases, including culturing the host cell.

The polynucleotide or the recombinant vector including the polynucleotide may be inserted into a host cell by using an insertion method widely known in the art. If the host cell is a prokaryotic cell, a $CaCl_2$ method and an electroporation method may be used. If the host cell is a eukaryotic cell, a microinjection method, a calcium phosphate precipitation method, an electroporation method, a liposome-mediated transfection method, or a gene bombardment method may be used. However, the method is not limited thereto. The method using a microorganism such as *E. coli* has a higher productivity than that using an animal cell, but it is not suitable for production of an intact Ig antibody due to glycosylation. However, the method can be used to produce an antigen-binding fragment such as Fab and Fv.

A method for screening the transformed host cells may be carried out easily according to a method widely known in the art by using a phenotype of a selectable marker. For example, when the selectable marker is a resistance gene to a specific antibiotic, a transformant may be selected easily by culturing the transformant in a medium including the antibiotic.

Further, yet another exemplary embodiment of the present disclosure provides a method for treating a target with a bone disease, including administering a peptide having an amino acid sequence of SEQ ID NO: 1 in a therapeutically effective amount to a target in need of help.

The peptide may be administered in the form of pharmaceutical composition. The peptide may be included in an amount of 0.001 to 30 wt. %, preferably 5 to 30 wt. %, and more preferably 5 to 20 wt. %, with respect to the total weight of the pharmaceutical composition.

The pharmaceutical composition of the present disclosure may further include a suitable carrier, excipient, and diluent typically used for production of a pharmaceutical composition. Further, the pharmaceutical composition of the present disclosure can be formulated and used in the form of oral injection such as powders, granules, tablets, capsules, suspensions, emulsions, syrups, aerosols, and the like, external preparations, suppositories, and sterile injection solutions according to a general method. Preferably, a suitable preparation known in the art may use those described in Remington's Pharmaceutical Science (recent version) [Mack Publishing Company, Easton Pa.]. Examples of the carrier, excipient, and diluent which can be included may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, and mineral oil. If the composition is formulated, a generally-used diluent or excipient such as a filler, an extender, a binder, a wetting agent, a disintegrating agent, a surfactant, and the like, may be used. Solid formulations for oral administration are tablets, pills, powders, granules, capsules, and the like, and the solid formulations are prepared by mixing at least one or more excipients, such as starch, calcium carbonate, sucrose, lactose, gelatin, and the like, into the composition. Further, not only the simple excipients but also lubricants such as magnesium stearate and talc may be used. Liquid formulations for oral administration are suspensions, solutions, emulsions and syrups, and may include various excipients such as wetting agents, sweeteners, aromatics and preservatives in addition to generally used simple diluents such as water and liquid paraffin. Formulations for parenteral administration include sterilized aqueous solutions, non-aqueous solvents, suspensions, emulsions, lyophilized formulations, suppositories, and the like. The non-aqueous solvents and suspensions may include propylene glycol, polyethylene glycol, vegetable oil such as olive oil, injectable ester like ethylolate, and the like. A base compound of the suppositories may include witepsol, macrogol, tween 61, cacao butter, laurin butter, glycerogelatin, and the like.

The term "administration" used herein refers to providing a predetermined peptide of the present disclosure or a pharmaceutical composition including the peptide by a certain suitable method to a subject.

The term "subject" used herein is a subject, preferably a mammal, in need of treatment or prevention of a bone disease. For example, the subject may be a dog, a pig, a cow, a horse, a sheep, a rabbit, a monkey, a cat, a mouse, a rat, and the like, and may be most preferably a human.

In the treatment of the present disclosure, the peptide or the pharmaceutical composition may be administered in an amount that elicits a biological or medicinal response in a tissue system, an animal, or a human that is being sought by a researcher, veterinarian, doctor or other clinician, i.e., a therapeutically effective amount that induces relief of symptoms of a disease or disorder to be treated. In the treatment of the present disclosure, it is obvious to those who are skilled in the art that an effective administration amount and a number of times of administration may be changed depending on a required effect. Therefore, an optimum dose to be administered can be easily determined by those who are skilled in the art, and can be controlled by various factors, such as a type of disease, severity of disease, the amounts of an active ingredient and other components included in a composition, a type of dosage form, and an age, a weight, a general health condition, a sex, and a diet of a patient, an administration time, an administration route, a secretion rate of a composition, a treatment period, a drug of simultaneous use, and the like. For a preferable effect, the peptide or the composition of the present disclosure may be administered in an amount of 0.05 to 0.1 mg/kg/day, preferably 0.01 to 0.1 mg/kg/day, and may be administered one time or several times per day.

In the treatment of the present disclosure, the peptide or the composition may be administered to the subject through various routes. All of administration methods are expectable. For example, the administration method may be carried out by oral dosage, rectal administration, or intravenous injection, intramuscular injection, hypodermic injection, intradural injection within the womb, or cerebrovascular injection.

Further, the treatment of the present disclosure may be used alone for preventing or treating bone diseases, or may be used in combination with surgery, radiation therapy, hormonal therapy, chemotherapy, or other methods using a biological response regulator.

Further, the peptide having an amino acid of SEQ ID NO: 1 of the present disclosure may be added to food in order to be used for preventing or improving bone diseases. If the peptide of the present disclosure is used as a food additive, the peptide may be appropriately used according to generally used methods by being added as it is or being mixed with other food or food ingredients.

The peptide as an active component may be appropriately changed in an amount depending on a usage purpose (prevention, health, or therapeutic treatment), and may be included in an amount of 0.001 to 30 wt. %, preferably 5 to 30 wt. %, and more preferably 5 to 20 wt. %, with respect to the total weight of food ingredients.

To be specific, for example, when food or beverage is produced, the peptide of the present disclosure may be added in an amount of 15 wt. % or less, preferably 10 wt. % or less, with respect to the material. However, for a long-time ingestion with a purpose of promoting health, hygiene or regulating health, the amount of the peptide may be less than the above-described range. Otherwise, since the peptide has no problem in view of safety, the amount may be greater than the above described range.

There is no specific limitation in the kind of the food. Examples of the food to be added with the peptide may include meat, sausage, bread, chocolate, candies, snacks, sweets, pizza, ramen, other noodles, gums, dairy foods including ice cream, various kinds of soups, beverages, teas, drink preparations, alcoholic beverages, and vitamin complexes, and may include all kinds of health functional food in an accepted meaning.

If a beverage including the peptide is produced, the beverage may include additional ingredient such as various flavoring agents or natural carbohydrates like general beverages. Examples of the natural carbohydrates include monosaccharides such as glucose and fructose; disaccharides such as maltose and sucrose; natural sweeteners such as dextrin and cyclodextrin, and synthetic sweeteners such as saccharin, aspartame, and the like.

In addition, the food for preventing or improving bone diseases of the present disclosure may include various nutritional supplements, vitamins, electrolytes, flavoring agents, colorants, pectic acid and its salt, alginic acid and its salt, organic acids, protective colloidal thickeners, pH regulating agents, stabilizers, preservatives, glycerin, alcohols, carbonizing agents used in carbonated drinks, and the like. Moreover, the food of the present disclosure may include fruit flesh for preparation of natural fruit juices, fruit juice beverages, and vegetable beverages. These ingredients may be used alone or in combination. Although a ratio of the additives is not strictly limited, these additives are generally included in an amount of 0.01 to 0.1 wt. % with respect to the total weight of the food of the present disclosure.

According to the exemplary embodiments of the present disclosure, the novel peptide of the present disclosure can induce mobilization of the hematopoietic stem cell to blood and cause a decrease in the number of osteoclasts, and, thus, decrease bone erosion caused by osteoclasts, thereby suppressing progress of an osteoporotic lesion. Further, the peptide of the present disclosure is safe since it does not cause rejection in the body. Furthermore, since the peptide is formed of 15 short amino acids, a low dose of the peptide can relieve symptoms of osteoporosis.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
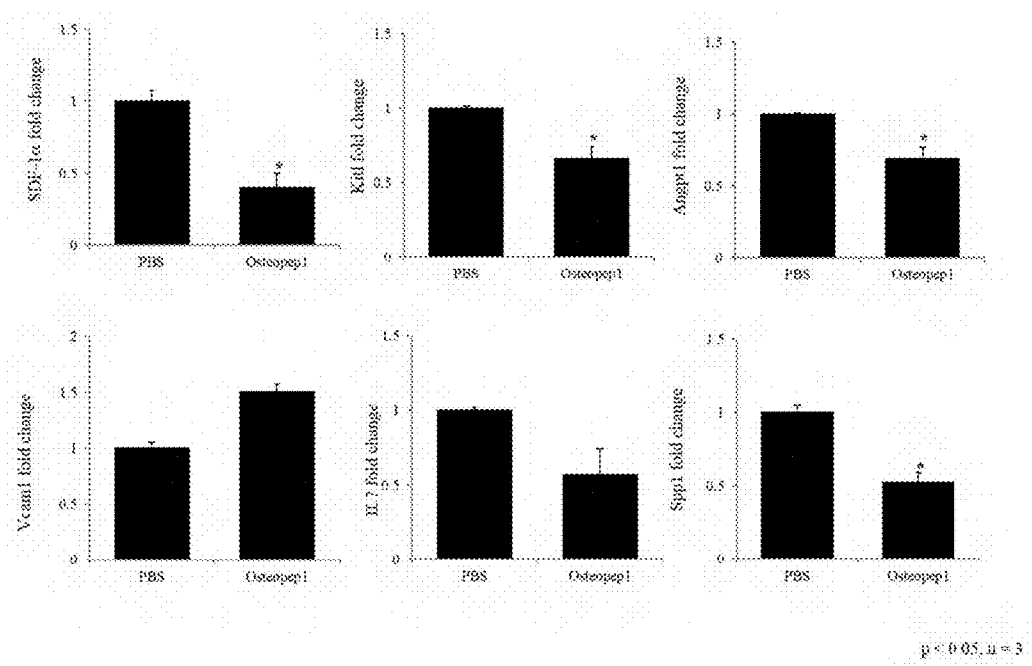
FIG. 1 is a diagram illustrating a change in an expression level of an adhesion factor for a bone marrow hematopoietic stem cell when Osteopep1 of the present disclosure is administered.

In the following detailed description, reference is made to the accompanying drawing, which forms a part hereof. The illustrative embodiments described in the detailed description, drawing, and claims are not meant to be limiting. Other embodiments may be utilized, and other changes may be made, without departing from the spirit or scope of the subject matter presented here.

Hereinafter, the present disclosure will be described in more detail with reference to Examples. However, Examples are provided for illustrative purposes only and not intended to limit the scope of the present disclosure.

Example 1

Materials for Experiment and Experiment Method 1-1. Preparation of Mice and Protocol of Drug Treatment All of the mice used in the experiment were 6-week- to 8-week-old C57BL/6 mice and purchase from Jackson Laboratory (Bar Harbor, Me., USA).

Osteopep1 used herein was produced by PEPTRON. For in vitro experiment, 0 nM Osteopep1 and 10 nM Osteopep1 were diluted in respective media and then injected. Further, for in vivo experiment, three mice per group, fifteen mice in total, were anesthetized with a mixed solution of 100 mg/kg of ketamine and 10 mg/kg of xylazine. Further, the each mouse was administered with 50 μg/kg of Osteopep1 and 100 μl of PBS (Gibco) by intravenous injection to its tail.

In order to prepare osteoporosis models, three 12-week-old female mice per group, six 12-week-old female mice in total, had an ovariectomy. After 1 week, 50 µg/kg of Osteopep1 (PEPTRON) and 100 µl of PBS (Gibco) were intraperitoneally administered every 12 hours twice per day for 3 weeks. For control groups as sham osteoporosis models, three female mice per group, six female mice in total, had a subcision.

1-2. Culturing of Bone Marrow Mesenchymal Stem Cell and Induction of Differentiation into Osteoblast After a 4-week- to 6-week-old C57BL/6 mouse was anesthetized and sacrificed, the tibias and the femurs were removed. Bone marrow was harvested from the tibias and the femurs, and a single cell suspension was obtained by using a 40 µm cell strainer (Becton-Dickinson LAβware, Franklin Lakes, N.J.). About $10^7$ cells were divided in a 75-cm² flask including Mesenchymal Stem Cell Stimulatory Supplements (Stem Cell Technologies, Inc.) added with antibiotics and MesenCult™ MSC Basal medium. After being cultured for one week, the cells were cultured for three weeks in StemXVivo Osteogenic/Adipogenic Base Media (R&D systems) added with StemXVivo Osteogenic supplement (20×) and penicillin-streptomycin (100×) for differentiation into osteoblasts. The culture media were replaced every 2 to 3 days.

1-3. Real-Time Quantitative PCR

In order to measure expression levels of adhesion factors (Sdf-1a, Kitl, Angpt1, IL7, Vcam1, Spp1) for hematopoietic stem cells present in osteoblasts, a real-time quantitative PCR was used.

An RNeasy Plus mini kit (Qiagen, Korea, Ltd.) was used to extract total RNA from a cell eluent and bone marrow cells. A kit produced by Clontech (Mountain View, Calif.) was used to synthesize cDNA from 5 µg of the total RNA. Further, a Corbett research RG-6000 real-time PCR device was used to perform a real-time quantitative PCR repeatedly for 40 cycles under a condition of 95° C. for 10 minutes; 95° C. for 10 seconds; 58° C. for 15 seconds; and 72° C. for 20 seconds per cycle.

Primers used in the real-time quantitative PCR were as listed in the following Table.

TABLE 1

| | | | SEQ ID NO: |
|---|---|---|---|
| SDF-1 α | F | 5'-TTCCTATCAGAGCCCATAGAG-3' | 2 |
| | R | 5'-CCAGACCATCCTGGATAATG-3' | 3 |
| Kit ligand (stem cell factor; SCF) | F | 5'-CCAAAAGCAAAGCCAATTACAAG-3' | 4 |
| | R | 5'-AGACTCGGGCCTACAATGGA-3' | 5 |
| Angiopoietin-1 (Angpt1) | F | 5'-ACGGGGGTCAATTCTAAG-3' | 6 |
| | R | 5'-GCCATTCCTGACTCCACA-3' | 7 |
| Vascular cell adhesion molecule-1 (Vcam1) | F | 5'-AAAAGCGGAGACAGGAGACA-3' | 8 |
| | R | 5'-AGCACGAGAAGCTCAGGAGA-3' | 9 |
| IL7 | F | 5'-ATTGAACCTGCAGACCAAGC-3' | 10 |
| | R | 5'-GCAACAGAACAAGGATCAGG-3' | 11 |
| Spp1 (osteopontin) | F | 5'-TGTGGAGTTTTAGAGATATTAGA TAGTGGG-3' | 12 |
| | R | 5'-AACA CACTCTTAACACCACTAAA TCACC-3' | 13 |
| GAPDH | F | 5'-TTGCTGTTGAAGTCGCAGGAG-3' | 14 |
| | R | 5'-TGTGTCCGTCGTGGATCTGA-3' | 15 |

1-4. Colony-Forming Unit (CFU) Assays

In order to measure the number of bone marrow hematopoietic progenitor cells in blood of a mouse, CFU assays were conducted.

A mouse was anesthetized, and then, 500 µl to 700 µl of blood was collected from the heart into a heparin tube. Then, the collected blood was put into an ammonium chloride solution (Stem Cell Technologies, Inc. 1:10) and then placed in ice for 15 minutes, and red blood cells were removed. The resultant solution was shaken every 2 to 3 minutes to remove red blood cells well, and then, centrifuged for 7 minutes at 1000 rpm. The supernatant was removed, and the resultant solution was washed with IMDM (Gibco) supplied with 2% fetal bovine serum (FBS) (Gibco). The washed cells ($3\times10^5$ per mouse) were divided into three 35 mm dishes ($1\times10^5$ per dish) respectively including methylcellulose-based media (Methocult, Stem cell), and then, cultured for 2 weeks. Then, the number of colonies in the flask was counted.

1-5. Flow Cytometry Analysis (FACs)

In order to find out any change in the number of bone marrow hematopoietic stem cells present in bone marrow of mice, Osteopep1 and PBS were injected to normal mice, respectively. After 60 minutes, bone marrow was harvested, and FACs was conducted to the harvested bone marrow by using three kinds of antibodies including Lineage, Sca-1, and c-kit as markers of bone marrow hematopoietic stem cells.

For analyzing bone marrow hematopoietic stem cells, red blood cells were removed from bone marrow, which was harvested from the tibias and the femurs of a 4-week- to 6-week-old C57BL/6 mouse, with an ammonium chloride solution (Stem Cell Technologies, Inc. 1:4) and then, the bone marrow was washed with a PBS (Gibco) solution including 10% fetal bovine serum (FBS) (Gibco) and 1% sodium azide (Sigma-Aldrich) and centrifuged for 10 minutes at 300×g. The hematopoietic cells included in the bone marrow were removed with MACs beads (Miltenyi Biotec) by using a biotinylated lineage antibody (Miltenyi Biotec), and the remaining cells were reacted at 4° C. for 30 minutes by using Sca-1-PECY7, c-kit-APC, CD150-PE, and CD48-FITC antibodies (BD science) and then analyzed with a flow cytometer LSRII (BD science).

1-6. Micro CT

The femurs was separated from the mouse and refrigerated in 80% ethanol. Then, for micro CT scanning, a tissue having a thickness of 40 µm was measured with a micro CT scanner (Inveon preclinical CT, Siemens Healthcare, Hoffman Estates, Ill.) under conditions including an exposure time of 600 msec, photon energy of 70 keV, and a current of 400 µA. In order to measure a bone density (bone volume/total volume) and a trabecular thickness, pieces each having a volume of 2.5×0.5×0 5 mm³ from the same site of each group were measured with Siemens Inveon Software.

Example 2

Effect of Osteopep1 on Expression of Adhesion Factor for Bone Marrow Hematopoietic Stem Cell and Number of Hematopoietic Stem Cells in Blood In order to find out an effect of Osteopep1 on expression of adhesion factors (Sdf-1a, Kitl, IL7, Vcam1, Spp1) for hematopoietic stem cells present in osteoblasts and the number of bone marrow hematopoietic progenitor cells in blood, the following experiment was conducted.

2-1. Expression Level of Adhesion Factor for Hematopoietic Stem Cell

In order to find out in vivo effects of Osteopep1 of the present disclosure on an expression level of an adhesion factor for a bone marrow hematopoietic stem cell, a mouse was administered with 50 µg/kg of Osteopep1 by intravenous injection to its tail, and after 60 minutes, bone marrow was harvested from the tibia and the femur of the mouse. Then, expression levels of the adhesion factors were checked by a real-time quantitative PCR.

The result thereof was as illustrated in FIG. 1.

As illustrated in FIG. 1, the expression levels of the main adhesion factors Sdf-1a, Kitl, Angpt1, and Spp1 were decreased ($p<0.05$, $n=3$ per group).

2-2. Measurement of Number of Bone Marrow Hematopoietic Progenitor Cells in Blood (CFU Assay)

In order to check whether mobilization of bone marrow hematopoietic progenitor cells to blood is induced by a decrease in expression level of the adhesion factors caused by administration of Osteopep1 of the present disclosure, a mouse was administered with 50 µg/kg of Osteopep1 by intravenous injection to its tail, and after 60 minutes, blood was collected from the heart. Then, a CFU (Colony-forming unit) assay was conducted thereto.

Figure 2:
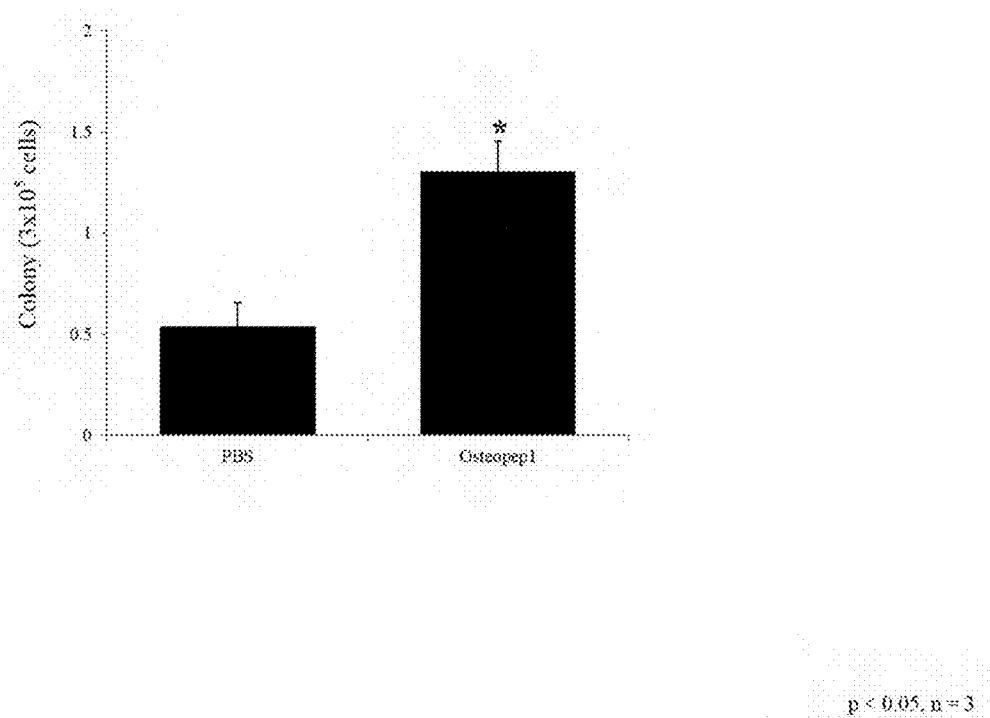
FIG. 2 is a diagram illustrating the number of bone marrow hematopoietic progenitor cells in blood when Osteopep1 of the present disclosure is administered.

The result thereof was as illustrated in FIG. 2.

As illustrated in FIG. 2, it could be seen that administration of Osteopep1 increased mobilization of bone marrow hematopoietic progenitor cells to blood ($p<0.05$, $n=3$ per group).

2-3. Measurement of Number of Bone Marrow Hematopoietic Stem Cells in Bone Marrow (FACs Assay)

In order to find out effects of administration of Osteopep1 of the present disclosure on the number of bone marrow hematopoietic stem cells present in bone marrow, the following experiment was conducted according to the method of Example 1-5.

Firstly, normal mice were divided into two groups each including 3 mice, and the respective groups were administered with 50 µg/kg of Osteopep1 and 100 µl of PBS (Gibco). After 60 minutes, bone marrow was harvested, and FACs was conducted to the harvested bone marrow by using three kinds of antibodies including Lineage, Sca-1, and c-kit as markers of bone marrow hematopoietic stem cells.

Figure 3:
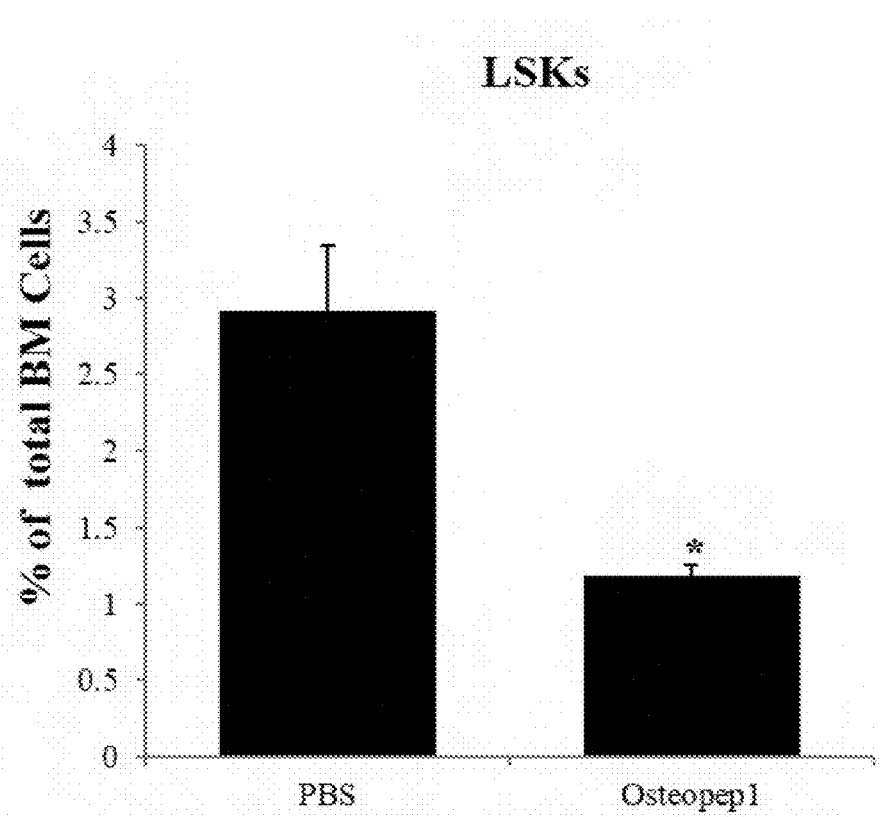
FIG. 3 is a diagram illustrating a mobilization level of Osteopep1 of the present disclosure to blood by using a marker of a bone marrow hematopoietic stem cell.

The result thereof was as illustrated in FIG. 3.

As illustrated in FIG. 3, the bone marrow hematopoietic stem cells marked by Lineage, Sca-1, and c-kit were decreased by administration of Osteopep1 rather than administration of PBS ($p<0.05$, $n=3$ per group).

Example 3

Effect of Osteopep1 of the Present Disclosure on Expression of Adhesion Factor for Hematopoietic Stem Cell In order to find out effects of Osteopep1 on an expression level of an adhesion factor involved in maintaining of bone marrow hematopoietic stem cell within bone marrow, the following experiment was conducted according to the method of Example 1-2 and Example 1-3.

Firstly, bone marrow was harvested from a 4-week- to 6-week-old C57BL/6 mouse, and bone marrow mesenchymal stem cells (BM-MSC) were collected and cultured for 3 weeks in bone cell differentiation-inducing medium and thus differentiated into osteoblasts. On the 21st day, the osteoblasts were treated with 0 nM Osteopep1 and 10 nM Osteopep1 for three days. Then, bone cells were collected, and expression levels of six kinds of adhesion factors were checked by a real-time quantitative PCR.

Figure 4:
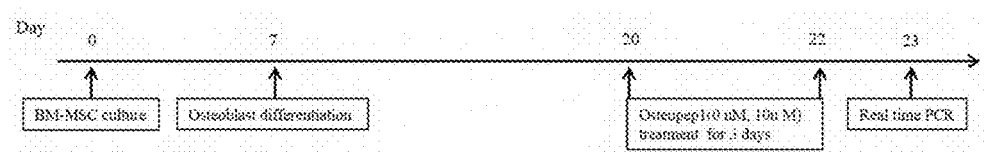
FIG. 4 illustrates an overview of an experiment conducted to find out an effect of Osteopep1 of the present disclosure on an expression level of an adhesion factor for a bone marrow hematopoietic stem cell.
Figure 5:
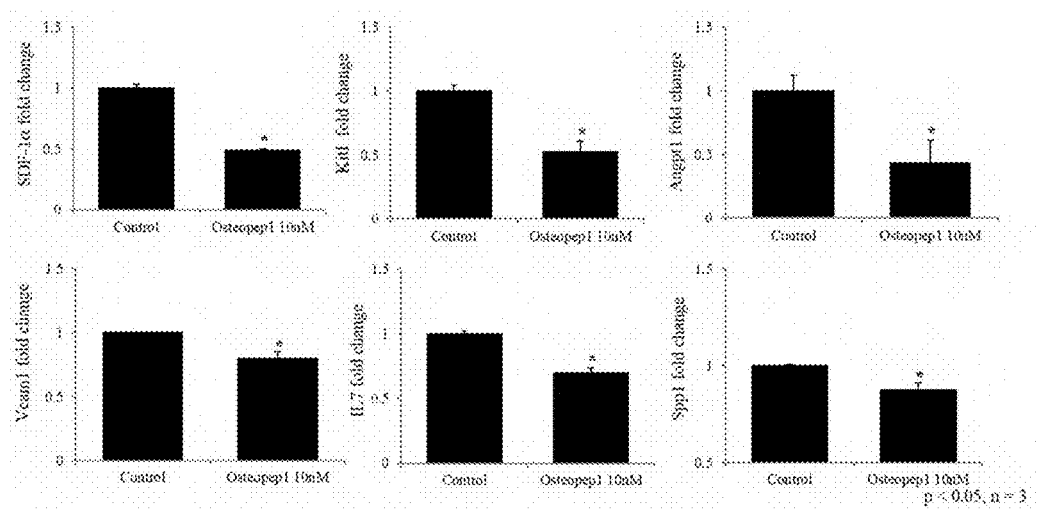
FIG. 5 illustrates a result of an effect of Osteopep1 of the present disclosure on an expression level of an adhesion factor for a bone marrow hematopoietic stem cell.

A mimetic diagram relevant to the experiment process was as illustrated in FIG. 4, and the measurement result of the expression levels of the adhesion factors was as illustrated in FIG. 5.

As illustrated in FIG. 5, it could be seen that as compared with the osteoblasts (Control) which were not treated with Osteopep1, the expression levels of Sdf-1a, Kitl, and Angpt1 in the osteoblasts treated with 0 nM Osteopep1 and 10 nM were concentration-dependently decreased ($p<0.05$, $n=3$ per group).

It could be seen from the above result that Osteopep1 decreased an expression level of an adhesion factor for a bone marrow hematopoietic stem cell present in an osteoblast, and, thus, mobilization of bone marrow hematopoietic stem cells to blood from bone marrow could be induced.

Example 4

Effect of Osteopep1 of the Present Disclosure on Prevention and Treatment of Osteoporosis In order to check whether mobilization of a hematopoietic stem cell to blood caused by administration of Osteopep1 of the present disclosure has an effect on prevention and treatment of osteoporosis, the following experiment was conducted according to the method of Example 1-1 and Example 1-6.

In order to prepare osteoporosis models, three 12-week-old female mice per group had an ovariectomy. After 1 week, 50 µg/kg of Osteopep1 (PEPTRON) and 100 µl of PBS (Gibco) were intraperitoneally administered every 12 hours twice per day for 3 weeks. For a control group, a normal mouse had a subcision and was intraperitoneally administered with 100 µl of PBS or 50 µg/kg of Osteopep1. On the 22nd day, the femurs was separated from the mouse and refrigerated in 80% ethanol. Then, a bone density and a trabecular thickness were measured by micro CT.

4-1. Effect of Osteopep1 on Expression of Adhesion Factor for Bone Marrow Hematopoietic Stem Cell in Osteoporosis Model In order to find out effects of Osteopep1 on an expression level of an adhesion factor involved in maintaining of bone marrow hematopoietic stem cell within bone marrow in an osteoporosis model, the following experiment was conducted according to the method of Example 1-3.

Figure 6:
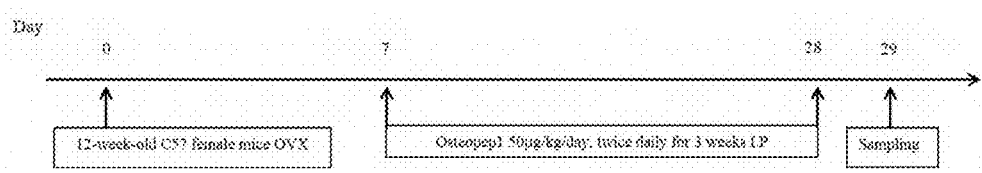
FIG. 6 illustrates an overview of an experiment conducted to find out an effect of Osteopep1 of the present disclosure on osteoporosis and treatment thereof.
Figure 7:
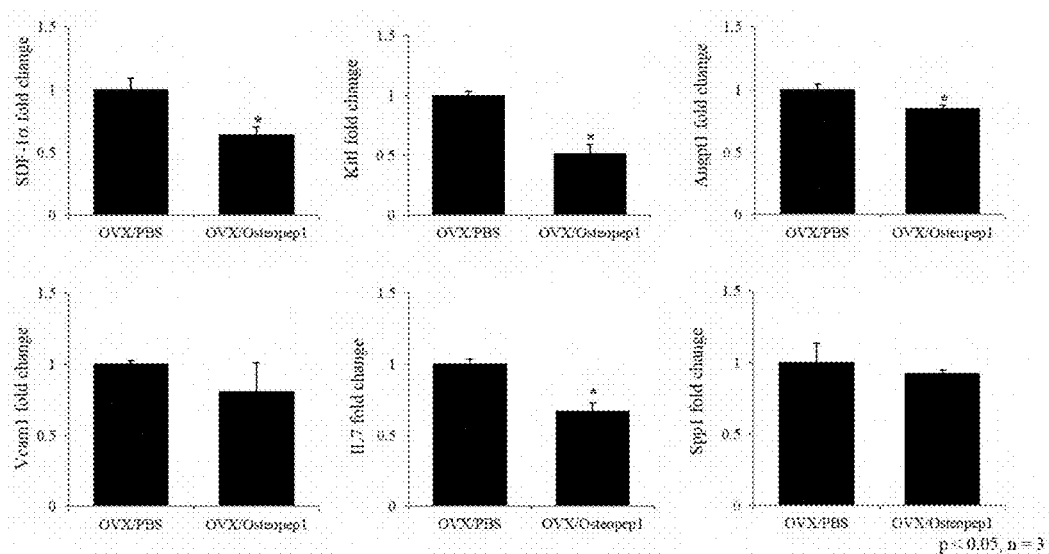
FIG. 7 is a diagram illustrating a change in an expression level of an adhesion factor for a bone marrow hematopoietic stem cell when Osteopep1 is administered to an osteoporosis model.

A mimetic diagram relevant to the experiment process was as illustrated in FIG. 6, and the result thereof was as illustrated in FIG. 7.

As illustrated in FIG. 7, when Osteopep1 was administered, the expression levels of the adhesion factors (Sdf-1a, Kitl, Angpt1, IL7, Vcam1, Spp1) for hematopoietic stem cells in the osteoporosis models were decreased ($p<0.05$, $n=3$ per group).

4-2. Effect of Osteopep1 on Mobilization of Bone Marrow Hematopoietic Progenitor Cell to Blood in Osteoporosis Model In order to find out effects of administration of Osteopep1 of the present disclosure on bone marrow hematopoietic progenitor cells mobilized to blood in an osteoporosis model, an experiment was conducted in the same manner as the method of Example 1-4.

Figure 8:
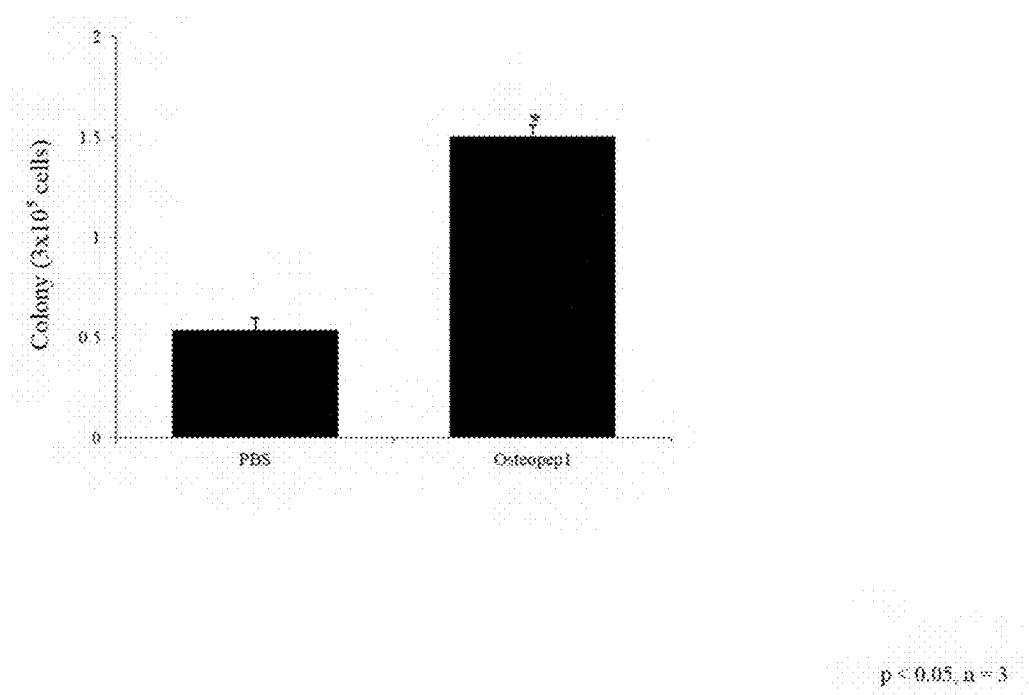
FIG. 8 is a diagram illustrating the number of bone marrow hematopoietic progenitor cells in blood when Osteopep1 is administered to an osteoporosis model.

The result thereof was as illustrated in FIG. 8.

As illustrated in FIG. 8, it could be seen that Osteopep1 increased mobilization of bone marrow hematopoietic progenitor cells to blood in the osteoporosis models ($p<0.05$, $n=3$ per group).

4-3. Effect of Osteopep1 on Mobilization of Bone Marrow Hematopoietic Progenitor Cell to Blood in Osteoporosis Model and Micro CT In order to check whether mobilization of bone marrow hematopoietic progenitor cells to blood in an osteoporosis model is induced by Osteopep1 of the present disclosure, the following experiment was conducted.

Figure 9:
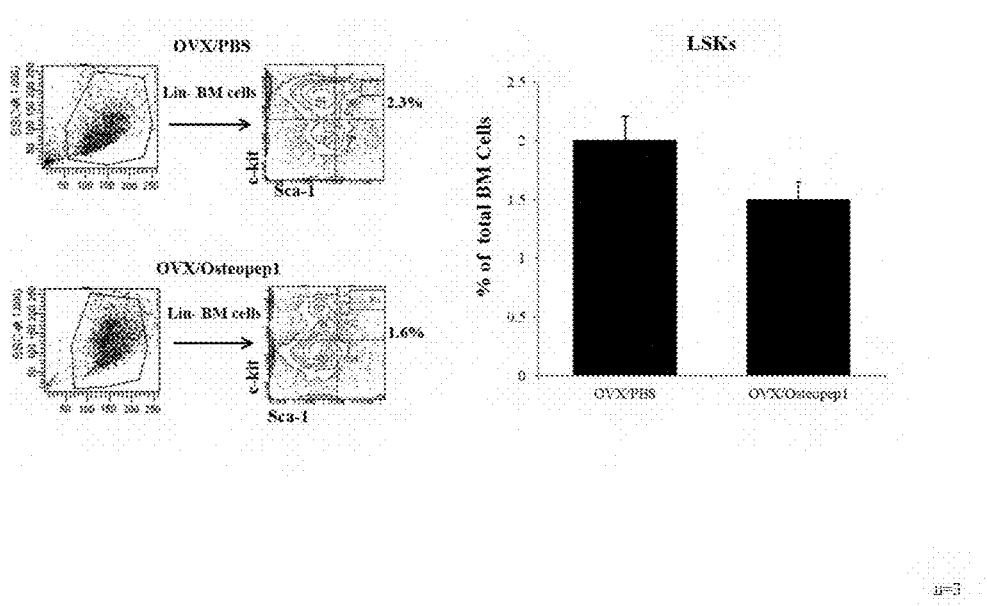
FIG. 9 is a diagram illustrating a mobilization level of bone marrow hematopoietic stem cells to blood when Osteopep1 is administered to an osteoporosis model, by using a marker of a bone marrow hematopoietic stem cell.

The result thereof was as illustrated in FIG. 9.

As illustrated in FIG. 9, the mobilized amounts of the markers of bone marrow hematopoietic stem cells were increased ($p<0.05$, n=3 per group).

It could be seen from the above result that a long-time administration of Osteopep1 of the present disclosure decreased an expression level of an adhesion factor for a bone marrow hematopoietic stem cell present in an osteoblast, and, thus, mobilization of bone marrow hematopoietic stem cells to blood could be induced.

Figure 10:
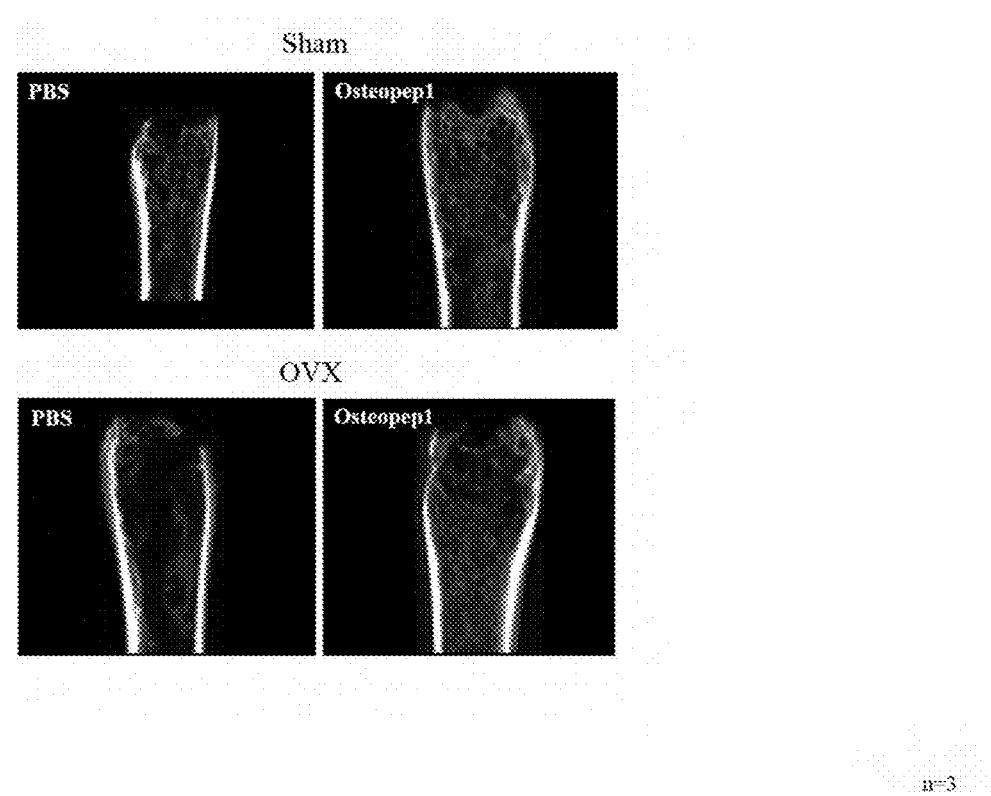
FIG. 10 provides micro CT images exhibiting an overall change in bone density when Osteopep1 is administered to an osteoporosis model.
Figure 11:
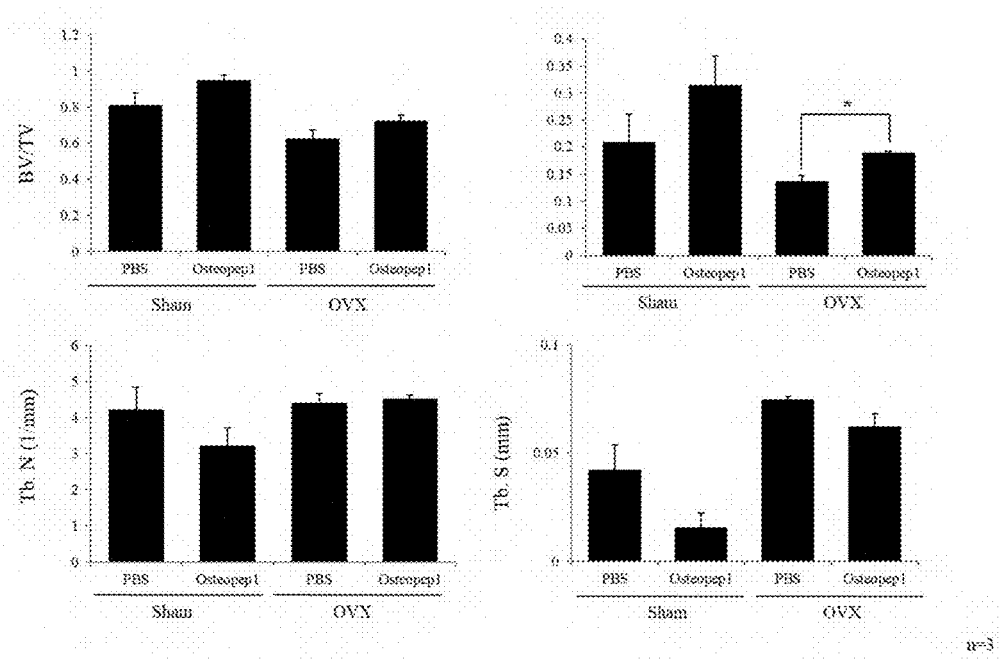
FIG. 11 provides graphs quantifying a change in bone density and a change in trabecular thickness, which are measured by micro CT, when Osteopep1 is administered to an osteoporosis model.

FIG. 10 provides micro CT images showing bone of a control group and an osteoporosis model, and FIG. 11 provides graphs exhibiting changes in bone density and trabecular thickness.

As shown in FIG. 10, it could be seen from the micro CT images that a bone density percentage (BV/TV, %) and a trabecular thickness (mm) of the osteoporosis model mouse injected with Osteopep1 were increased as compared with the osteoporosis model mouse injected with PBS, and a similar tendency was observed in the control group models (n=3 per group).

It can be seen from the above result that mobilization of bone marrow hematopoietic stem cells to blood caused by a long-time administration of Osteopep1 to a mouse with osteoporosis induces differentiation from a hematopoietic stem cell into osteoclasts and a decrease in the number of osteoclasts within bone marrow, and, thus, it is possible to suppress decreases in bone density and trabecular thickness in the mouse with osteoporosis.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

---

What is claimed is:

1. A method for treating a subject with osteoporosis, comprising:

administering a peptide consisting of the amino acid sequence of SEQ ID NO: 1 in a therapeutically effective amount to the subject in need thereof.

2. The method of claim 1, wherein the peptide decreases the expression level of an adhesion factor for a bone marrow hematopoietic stem cell and mobilizes the bone marrow hematopoietic stem cell in bone marrow to bloodstream.

3. The method of claim 1, wherein the peptide decreases the number of osteoclasts in the bone marrow of the subject.

* * * * *